United States Patent [19]

Moore et al.

[11] Patent Number: 5,686,574
[45] Date of Patent: Nov. 11, 1997

[54] CONSTITUTIVE ACTIVATOR OF RETINOID ACID RESPONSE (CAR) RECEPTOR FUSION PROTIEN

[75] Inventors: David D. Moore, Hingham; Myriam L. Baes, Belmont, both of Mass.

[73] Assignee: The General Hospital Corporation, Boston, Mass.

[21] Appl. No.: 459,489

[22] Filed: Jun. 5, 1995

Related U.S. Application Data

[62] Division of Ser. No. 843,350, Feb. 26, 1992.

[51] Int. Cl.$^6$ .................. C07K 14/435; C12N 15/62; C12N 15/00; C12P 21/00
[52] U.S. Cl. .................. 530/350; 536/23.4; 435/69.1; 435/69.7
[58] Field of Search ...................... 530/350; 514/2; 435/69.1, 69.7; 536/23.4

[56] References Cited

U.S. PATENT DOCUMENTS

| | | | |
|---|---|---|---|
| 4,870,009 | 9/1989 | Evans et al. | 435/70 |
| 4,981,784 | 1/1991 | Evans et al. | 435/6 |
| 5,071,773 | 12/1991 | Evans et al. | 436/501 |
| 5,077,211 | 12/1991 | Yarosh | 435/193 |
| 5,183,736 | 2/1993 | Pfahl et al. | 435/6 |
| 5,571,696 | 11/1996 | Evans et al. | 435/69.1 |

FOREIGN PATENT DOCUMENTS

| | | |
|---|---|---|
| WO 91/12258 | 8/1898 | WIPO |
| WO 90/06318 | 6/1990 | WIPO |
| WO 90/07517 | 7/1990 | WIPO |
| WO 90/11273 | 10/1990 | WIPO |
| WO 90/14356 | 11/1990 | WIPO |
| WO 90/15815 | 12/1990 | WIPO |
| WO 91/07488 | 5/1991 | WIPO |
| WO 91/14695 | 10/1991 | WIPO |

OTHER PUBLICATIONS

Godowski et al. (1988) Science 241: 812–816.
Ma et al. (1987) Cell 48:847–853.
Sadowski et al. (1988) Nature 335:563–564.
Evans, "The Steroid and Thyroid Hormone Receptor Superfamily", Science 240:889–895, 1988.
Fuller, "The Steroid Receptor Superfamily: Mechanisms of Diversity", FASEB 5:3092–3099, 1991.
Gebert et al., "High Frequency of Retinoic Acid Receptor β Abnormalitites in Human Lung Cancer", Oncogene 6:1859–1868, 1991.
Kumar et al., "Functional Domains of the Human Estrogen Receptor", Cell 51:941–951, 1987.

*Primary Examiner*—Stephen Walsh
*Assistant Examiner*—Michael D. Pak
*Attorney, Agent, or Firm*—Clark & Elbing LLP

[57] ABSTRACT

Purified DNA encoding a Constitutive Activator of Retinoid acid response (CAR) receptors and the recombinant proteins expressed from such DNA are disclosed. The recombinant receptor polypeptides are members of the nuclear hormone receptor super family and are used to identify CAR ligands and CAR receptor binding sites and are also used to produce therapeutics. Antibodies specific for CAR receptor polypeptides are also disclosed.

7 Claims, 2 Drawing Sheets

GTGAGCTTGC TCCTTAAGTT ACAGGAACTC TCCTTATAAT AGACACTTCA TTTTCCTAGT

CCATCCCTCA TGAAAAATGA CTGACCACTG CTGGGCAGCA GGAGGGATGA TAATCCTAAC

TCCAATCACT GGCAACTCCT GAGATCAGAG GAAAACCAGC AACAGCGTGG GAGTTTGGGG

AGAGGCATTC CATACCAGAT TCTGTGGCCT GCAGGTGACA TGCTGCCTAA GAGAAGCAGG

AGTCTGTGAC AGCCACCCCA ACACGTGACG TC

| | | | | | | | | | | | | | | |
|---|---|---|---|---|---|---|---|---|---|---|---|---|---|---|
| ATG | GCC | AGT | AGG | GAA | GAT | GAG | CTG | AGG | AAC | TGT | GTG | GTA | TGT | GGG | GAC |
| Met | Ala | Ser | Arg | Glu | Asp | Glu | Leu | Arg | Asn | Cys | Val | Val | Cys | Gly | Asp |
| 1 | | | | 5 | | | | | 10 | | | | | 15 | |

| CAA | GCC | ACA | GGC | TAC | CAC | TTT | AAT | GCG | CTG | ACT | TGT | GAG | GGC | TGC | AAG |
|---|---|---|---|---|---|---|---|---|---|---|---|---|---|---|---|
| Gln | Ala | Thr | Gly | Tyr | His | Phe | Asn | Ala | Leu | Thr | Cys | Glu | Gly | Cys | Lys |
| | | | 20 | | | | | 25 | | | | | 30 | | |

| GGT | TTC | TTC | AGG | AGA | ACA | GTC | AGC | AAA | AGC | ATT | GGT | CCC | ACC | TGC | CCC |
|---|---|---|---|---|---|---|---|---|---|---|---|---|---|---|---|
| Gly | Phe | Phe | Arg | Arg | Thr | Val | Ser | Lys | Ser | Ile | Gly | Pro | Thr | Cys | Pro |
| | | 35 | | | | | 40 | | | | | 45 | | | |

| TTT | GCT | GGA | AGC | TGT | GAA | GTC | AGC | AAG | ACT | CAG | AGG | CGC | CAC | TGC | CCA |
|---|---|---|---|---|---|---|---|---|---|---|---|---|---|---|---|
| Phe | Ala | Gly | Ser | Cys | Glu | Val | Ser | Lys | Thr | Gln | Arg | Arg | His | Cys | Pro |
| | | 50 | | | | | 55 | | | | | 60 | | | |

| GCC | TGC | AGG | TTG | CAG | AAG | TGC | TTA | GAT | GCT | GGC | ATG | AGG | AAA | GAC | ATG |
|---|---|---|---|---|---|---|---|---|---|---|---|---|---|---|---|
| Ala | Cys | Arg | Leu | Gln | Lys | Cys | Leu | Asp | Ala | Gly | Met | Arg | Lys | Asp | Met |
| 65 | | | | 70 | | | | | 75 | | | | | 80 | |

| ATA | CTG | TCG | GCA | GAA | GCC | CTG | GCA | TTG | CGG | CGA | GCA | AAG | CAG | GCC | CAG |
|---|---|---|---|---|---|---|---|---|---|---|---|---|---|---|---|
| Ile | Leu | Ser | Ala | Glu | Ala | Leu | Ala | Leu | Arg | Arg | Ala | Lys | Gln | Ala | Gln |
| | | | | 85 | | | | | 90 | | | | | 95 | |

| CGG | CGG | GCA | CAG | CAA | ACA | CCT | GTG | CAA | CTG | AGT | AAG | GAG | CAA | GAA | GAG |
|---|---|---|---|---|---|---|---|---|---|---|---|---|---|---|---|
| Arg | Arg | Ala | Gln | Gln | Thr | Pro | Val | Gln | Leu | Ser | Lys | Glu | Gln | Glu | Glu |
| | | | | 100 | | | | | 105 | | | | | 110 | |

| CTG | ATC | CGG | ACA | CTC | CTG | GGG | GCC | CAC | ACC | CGC | CAC | ATG | GGC | ACC | ATG |
|---|---|---|---|---|---|---|---|---|---|---|---|---|---|---|---|
| Leu | Ile | Arg | Thr | Leu | Leu | Gly | Ala | His | Thr | Arg | His | Met | Gly | Thr | Met |
| | | 115 | | | | | 120 | | | | | 125 | | | |

| TTT | GAA | CAG | TTT | GTG | CAG | TTT | AGG | CCT | CCA | GCT | CAT | CTG | TTC | ATC | CAT |
|---|---|---|---|---|---|---|---|---|---|---|---|---|---|---|---|
| Phe | Glu | Gln | Phe | Val | Gln | Phe | Arg | Pro | Pro | Ala | His | Leu | Phe | Ile | His |
| | 130 | | | | | 135 | | | | | 140 | | | | |

| CAC | CAG | CCC | TTG | CCC | ACC | CTG | GCC | CCT | GTG | CTG | CCT | CTG | GTC | ACA | CAC |
|---|---|---|---|---|---|---|---|---|---|---|---|---|---|---|---|
| His | Gln | Pro | Leu | Pro | Thr | Leu | Ala | Pro | Val | Leu | Pro | Leu | Val | Thr | His |
| 145 | | | | 150 | | | | | 155 | | | | | 160 | |

| TTC | GCA | GAC | ATC | AAC | ACT | TTC | ATG | GTA | CTG | CAA | GTC | ATC | AAG | TTT | ACT |
|---|---|---|---|---|---|---|---|---|---|---|---|---|---|---|---|
| Phe | Ala | Asp | Ile | Asn | Thr | Phe | Met | Val | Leu | Gln | Val | Ile | Lys | Phe | Thr |
| | | | | 165 | | | | | 170 | | | | | 175 | |

FIG. 1

(PAGE 1 OF 2)

```
AAG GAC CTG CCC GTC TTC CGT TCC CTG CCC ATT GAA GAC CAG ATC TCC
Lys Asp Leu Pro Val Phe Arg Ser Leu Pro Ile Glu Asp Gln Ile Ser
            180             185             190

CTT CTC AAG GGA GCA GCT GTG GAA ATC TGT CAC ATC GTA CTC AAT ACC
Leu Leu Lys Gly Ala Ala Val Glu Ile Cys His Ile Val Leu Asn Thr
        195             200             205

ACT TTC TGT CTC CAA ACA CAA AAC TTC CTC TGC GGG CCT CTT CGC TAC
Thr Phe Cys Leu Gln Thr Gln Asn Phe Leu Cys Gly Pro Leu Arg Tyr
    210             215             220

ACA ATT GAA GAT GGA GCC CGT GTG GGG TTC CAG GTA GAG TTT TTG GAG
Thr Ile Glu Asp Gly Ala Arg Val Gly Phe Gln Val Glu Phe Leu Glu
225             230             235             240

TTG CTC TTT CAC TTC CAT GGA ACA CTA CGA AAA CTG CAG CTC CAA GAG
Leu Leu Phe His Phe His Gly Thr Leu Arg Lys Leu Gln Leu Gln Glu
            245             250             255

CCT GAG TAT GTG CTC TTG GCT GCC ATG GCC CTG TTC TCT CCT GAC CGA
Pro Glu Tyr Val Leu Leu Ala Ala Met Ala Leu Phe Ser Pro Asp Arg
        260             265             270

CCT GGA GTT ACC CAG AGA GAT GAG ATT GAT CAG CTG CAA GAG GAG ATG
Pro Gly Val Thr Gln Arg Asp Glu Ile Asp Gln Leu Gln Glu Glu Met
    275             280             285

GCA CTG ACT CTG CAA AGC TAC ATC AAG GGC CAG CAG CGA AGG CCC CGG
Ala Leu Thr Leu Gln Ser Tyr Ile Lys Gly Gln Gln Arg Arg Pro Arg
290             295             300

GAT CGG TTT CTG TAT GCG AAG TTG CTA GGC CTG CTG GCT GAG CTC CGG
Asp Arg Phe Leu Tyr Ala Lys Leu Leu Gly Leu Leu Ala Glu Leu Arg
305             310             315             320

AGC ATT AAT GAG GCC TAC GGG TAC CAA ATC CAG CAC ATC CAG GGC CTG
Ser Ile Asn Glu Ala Tyr Gly Tyr Gln Ile Gln His Ile Gln Gly Leu
            325             330             335

TCT GCC ATG ATG CCG CTG CTC CAG GAG ATC TGC AGC TGA GGCCATGCTC
Ser Ala Met Met Pro Leu Leu Gln Glu Ile Cys Ser
        340             345

ACTTCCTTCC CCAGCTCACC TGGAACACCC TGGATACACT GGAGTGGGAA

AATGCTGGGA CCAAAGATTG GCCGGGTTC AAAGGGAGCC CAGTGGTTGC AATGAAAGAC

TAAAGCAAAA C
```

FIG. 1

SEQUENCE LISTING ( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:
        ( A ) LENGTH: 1450
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
GTGAGCTTGC  TCCTTAAGTT  ACAGGAACTC  TCCTTATAAT  AGACACTTCA  TTTTCCTAGT     60

CCATCCCTCA  TGAAAAATGA  CTGACCACTG  CTGGGCAGCA  GGAGGGATGA  TAATCCTAAC    120

TCCAATCACT  GGCAACTCCT  GAGATCAGAG  GAAAACCAGC  AACAGCGTGG  GAGTTTGGGG    180

AGAGGCATTC  CATACCAGAT  TCTGTGGCCT  GCAGGTGACA  TGCTGCCTAA  GAGAAGCAGG    240

AGTCTGTGAC  AGCCACCCCA  ACACGTGACG  TCATGGCCAG  TAGGGAAGAT  GAGCTGAGGA    300

ACTGTGTGGT  ATGTGGGGAC  CAAGCCACAG  GCTACCACTT  TAATGCGCTG  ACTTGTGAGG    360

GCTGCAAGGG  TTTCTTCAGG  AGAACAGTCA  GCAAAAGCAT  TGGTCCCACC  TGCCCCTTTG    420

CTGGAAGCTG  TGAAGTCAGC  AAGACTCAGA  GGCGCCACTG  CCCAGCCTGC  AGGTTGCAGA    480

AGTGCTTAGA  TGCTGGCATG  AGGAAAGACA  TGATACTGTC  GGCAGAAGCC  CTGGCATTGC    540

GGCGAGCAAA  GCAGGCCCAG  CGGCGGGCAC  AGCAAACACC  TGTGCAACTG  AGTAAGGAGC    600

AAGAAGAGCT  GATCCGGACA  CTCCTGGGGG  CCCACACCCG  CCACATGGGC  ACCATGTTTG    660

AACAGTTTGT  GCAGTTTAGG  CCTCCAGCTC  ATCTGTTCAT  CCATCACCAG  CCCTTGCCCA    720

CCCTGGCCCC  TGTGCTGCCT  CTGGTCACAC  ACTTCGCAGA  CATCAACACT  TTCATGGTAC    780

TGCAAGTCAT  CAAGTTTACT  AAGGACCTGC  CCGTCTTCCG  TTCCCTGCCC  ATTGAAGACC    840

AGATCTCCCT  TCTCAAGGGA  GCAGCTGTGG  AAATCTGTCA  CATCGTACTC  AATACCACTT    900

TCTGTCTCCA  AACACAAAAC  TTCCTCTGCG  GGCCTCTTCG  CTACACAATT  GAAGATGGAG    960

CCCGTGTGGG  GTTCCAGGTA  GAGTTTTTGG  AGTTGCTCTT  TCACTTCCAT  GGAACACTAC   1020

GAAAACTGCA  GCTCCAAGAG  CCTGAGTATG  TGCTCTTGGC  TGCCATGGCC  CTGTTCTCTC   1080

CTGACCGACC  TGGAGTTACC  CAGAGAGATG  AGATTGATCA  GCTGCAAGAG  GAGATGGCAC   1140

TGACTCTGCA  AAGCTACATC  AAGGGCCAGC  AGCGAAGGCC  CCGGGATCGG  TTTCTGTATG   1200
```

| | | | | | |
|---|---|---|---|---|---|
| CGAAGTTGCT | AGGCCTGCTG | GCTGAGCTCC | GGAGCATTAA | TGAGGCCTAC | GGGTACCAAA | 1260
| TCCAGCACAT | CCAGGGCCTG | TCTGCCATGA | TGCCGCTGCT | CCAGGAGATC | TGCAGCTGAG | 1320
| GCCATGCTCA | CTTCCTTCCC | CAGCTCACCT | GGAACACCCT | GGATACACTG | GAGTGGGAAA | 1380
| ATGCTGGGAC | CAAAGATTGG | GCCGGGTTCA | AAGGGAGCCC | AGTGGTTGCA | ATGAAAGACT | 1440
| AAAGCAAAAC | | | | | | 1450

( 2 ) INFORMATION FOR SEQ ID NO: 2:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( x i ) SEQUENCE DESCRIPTION: SEQ ID NO: 2:

TGYGAGGGNT GYAAGGSNTT YTTYMG                              26

( 2 ) INFORMATION FOR SEQ ID NO: 3:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( x i ) SEQUENCE DESCRIPTION: SEQ ID NO: 3:

AAAGGTAAGA TCAGGGACGT GACCGCAG                           28

( 2 ) INFORMATION FOR SEQ ID NO: 4:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( x i ) SEQUENCE DESCRIPTION: SEQ ID NO: 4:

TGGGTGAATG AGGACATTAC TGACCGCTCC G                     31

( 2 ) INFORMATION FOR SEQ ID NO: 5:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( x i ) SEQUENCE DESCRIPTION: SEQ ID NO: 5:

GGGTAGGGTT CACCGAAAGT TCACTCG                           27

( 2 ) INFORMATION FOR SEQ ID NO: 6:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( x i ) SEQUENCE DESCRIPTION: SEQ ID NO: 6:

AAAGGTAAGA TCAGGGACGT GACCTCAG                           28

( 2 ) INFORMATION FOR SEQ ID NO: 7:

( i ) SEQUENCE CHARACTERISTICS:

( A ) LENGTH: 30
                    ( B ) TYPE: nucleic acid
                    ( C ) STRANDEDNESS: single
                    ( D ) TOPOLOGY: linear ( x i ) SEQUENCE DESCRIPTION: SEQ ID NO: 7:

CTGGAGGTGA CAGGAGGACA GCAGCCCTGA                                                           30

( 2 ) INFORMATION FOR SEQ ID NO: 8:

( i ) SEQUENCE CHARACTERISTICS:
                    ( A ) LENGTH: 44
                    ( B ) TYPE: nucleic acid
                    ( C ) STRANDEDNESS: single
                    ( D ) TOPOLOGY: linear ( x i ) SEQUENCE DESCRIPTION: SEQ ID NO: 8:

AGACAGGTTG ACCCTTTTTC TAAGGGCTTA ACCTAGCTCA CCTG                                            44

( 2 ) INFORMATION FOR SEQ ID NO: 9:

( i ) SEQUENCE CHARACTERISTICS:
                    ( A ) LENGTH: 28
                    ( B ) TYPE: nucleic acid
                    ( C ) STRANDEDNESS: single
                    ( D ) TOPOLOGY: linear ( x i ) SEQUENCE DESCRIPTION: SEQ ID NO: 9:

AGGACGTTGG GGTTAGGGGA GGACAGTG                                                             28

( 2 ) INFORMATION FOR SEQ ID NO: 10:

( i ) SEQUENCE CHARACTERISTICS:
                    ( A ) LENGTH: 348
                    ( B ) TYPE: amino acid
                    ( C ) STRANDEDNESS: Not Relevant
                    ( D ) TOPOLOGY: linear ( x i ) SEQUENCE DESCRIPTION: SEQ ID NO: 10:

```
Met  Ala  Ser  Arg  Glu  Asp  Glu  Leu  Arg  Asn  Cys  Val  Val  Cys  Gly  Asp
1              5                        10                       15

Gln  Ala  Thr  Gly  Tyr  His  Phe  Asn  Ala  Leu  Thr  Cys  Glu  Gly  Cys  Lys
               20                       25                       30

Gly  Phe  Phe  Arg  Arg  Thr  Val  Ser  Lys  Ser  Ile  Gly  Pro  Thr  Cys  Pro
          35                       40                       45

Phe  Ala  Gly  Ser  Cys  Glu  Val  Ser  Lys  Thr  Gln  Arg  Arg  His  Cys  Pro
     50                       55                       60

Ala  Cys  Arg  Leu  Gln  Lys  Cys  Leu  Asp  Ala  Gly  Met  Arg  Lys  Asp  Met
65                       70                       75                       80

Ile  Leu  Ser  Ala  Glu  Ala  Leu  Ala  Leu  Arg  Arg  Ala  Lys  Gln  Ala  Gln
               85                       90                       95

Arg  Arg  Ala  Gln  Gln  Thr  Pro  Val  Gln  Leu  Ser  Lys  Glu  Gln  Glu  Glu
               100                      105                      110

Leu  Ile  Arg  Thr  Leu  Leu  Gly  Ala  His  Thr  Arg  His  Met  Gly  Thr  Met
          115                      120                      125

Phe  Glu  Gln  Phe  Val  Gln  Phe  Arg  Pro  Pro  Ala  His  Leu  Phe  Ile  His
     130                      135                      140

His  Gln  Pro  Leu  Pro  Thr  Leu  Ala  Pro  Val  Leu  Pro  Leu  Val  Thr  His
145                      150                      155                      160

Phe  Ala  Asp  Ile  Asn  Thr  Phe  Met  Val  Leu  Gln  Val  Ile  Lys  Phe  Thr
               165                      170                      175

Lys  Asp  Leu  Pro  Val  Phe  Arg  Ser  Leu  Pro  Ile  Glu  Asp  Gln  Ile  Ser
```

|  | 180 |  |  |  |  |  | 185 |  |  |  | 190 |  |  |
|---|---|---|---|---|---|---|---|---|---|---|---|---|---|
| Leu | Leu | Lys 195 | Gly | Ala | Ala | Val | Glu 200 | Ile | Cys | His | Ile | Val 205 | Leu | Asn | Thr |
| Thr | Phe 210 | Cys | Leu | Gln | Thr | Gln 215 | Asn | Phe | Leu | Cys | Gly 220 | Pro | Leu | Arg | Tyr |
| Thr 225 | Ile | Glu | Asp | Gly | Ala 230 | Arg | Val | Gly | Phe | Gln 235 | Val | Glu | Phe | Leu | Glu 240 |
| Leu | Leu | Phe | His | Phe 245 | His | Gly | Thr | Leu | Arg 250 | Lys | Leu | Gln | Leu | Gln 255 | Glu |
| Pro | Glu | Tyr | Val 260 | Leu | Leu | Ala | Ala | Met 265 | Ala | Leu | Phe | Ser | Pro 270 | Asp | Arg |
| Pro | Gly | Val 275 | Thr | Gln | Arg | Asp | Glu 280 | Ile | Asp | Gln | Leu | Gln 285 | Glu | Glu | Met |
| Ala | Leu 290 | Thr | Leu | Gln | Ser | Tyr 295 | Ile | Lys | Gly | Gln | Gln 300 | Arg | Arg | Pro | Arg |
| Asp 305 | Arg | Phe | Leu | Tyr | Ala 310 | Lys | Leu | Leu | Gly | Leu 315 | Leu | Ala | Glu | Leu | Arg 320 |
| Ser | Ile | Asn | Glu | Ala 325 | Tyr | Gly | Tyr | Gln | Ile 330 | Gln | His | Ile | Gln 335 | Gly | Leu |
| Ser | Ala | Met | Met 340 | Pro | Leu | Leu | Gln | Glu 345 | Ile | Cys | Ser |

CONSTITUTIVE ACTIVATOR OF RETINOID ACID RESPONSE (CAR) RECEPTOR FUSION PROTIEN

This is a divisional of copending application Ser. No. 07/843,350, filed Feb. 26, 1992.

BACKGROUND OF THE INVENTION

This invention relates to receptors, particularly nuclear hormone receptors.

In higher organisms, the nuclear hormone receptor superfamily includes approximately a dozen distinct genes that encode zinc finger transcription factors, each of which is specifically activated by binding a ligand such as a steroid, thyroid hormone (T3) or retinoic acid (RA). However, there is an additional, somewhat larger group of cDNAs that encode proteins that do not bind or respond to any known ligand. These members of the superfamily are called orphan receptors. While the role of the better characterized conventional receptors in regulating important processes in developing and adult individuals is becoming clearer, the function of the orphan receptors has been uncertain.

A number of the conventional and orphan members of the superfamily share identical or very similar amino acid sequences in an important region of the first zinc finger. Both genetic analyses and X-ray crystallography indicate that this region, termed the P box, makes sequence specific contacts with the DNA. The conventional receptors in this P box-defined subgroup include those that bind estrogen, vitamin D, T3 and RA, and nearly all of the orphan receptors identified to date also fall into this class. As a consequence of this overlap in binding specificity, many hormone response elements can bind more than one type of receptor. The best characterized of these is the element upstream of the rat growth hormone gene, which can be activated by three different isoforms of the T3 receptor encoded by two different genes and by an unknown number of retinoic acid receptor isoforms encoded by three different genes. While it does not appear to respond to the estrogen receptor or the vitamin D receptor, its response to other members Of the subgroup remains uncertain.

Recently the potential complexity of the interactions of the conventional receptors with their response elements has been substantially increased by the demonstration that the three closely related RXR proteins can form heterodimers with the thyroid hormone, retinoic acid and vitamin D receptors. These heterodimers show higher binding affinity for appropriate response elements, and the RXRs are hypothesized to play central roles in signal transduction by all three classes of receptors. The impact on such heterodimers of the binding of the retinoid metabolite 9-cis retinoic acid by the RXRs remains unclear.

SUMMARY OF THE INVENTION

In general, the invention features substantially pure CAR receptor polypeptide. Preferably, such a receptor polypeptide includes an amino acid sequence substantially identical to the amino acid sequence shown in FIG. 1 (SEQ ID NO: 1).

The invention further features a substantially pure polypeptide which includes a CAR receptor DNA binding domain and a CAR receptor gene activation domain. Preferably, the DNA binding domain includes a sequence substantially identical to amino acids 11–75 of FIG. 1 (SEQ ID NO: 10), or a DNA binding fragment thereof; and the gene activation domain includes a sequence substantially identical to amino acids 76–348 of FIG. 1 (SEQ ID NO: 10), or a gene activating fragment thereof.

In a related aspect, the invention features a substantially pure polypeptide which includes a CAR receptor heterodimerization domain.

In preferred embodiments of various aspects, the receptor polypeptide is mammalian, and preferably, human.

In yet other aspects, the invention features substantially pure DNA which encodes a CAR receptor polypeptide of the invention. Preferably, such DNA is cDNA; and encodes a human CAR receptor polypeptide. The invention also features a vector which includes such substantially pure DNA and which is capable of directing expression of the protein encoded by the DNA in a vector-containing cell. Finally, the invention features a cell which contains the substantially pure DNA. Preferably, the cell is a eukaryotic cell, for example, a mammalian cell.

In another aspect, the invention features a method of producing a recombinant CAR receptor polypeptide (or a fragment or analog thereof). The method involves (a) providing a cell transformed with DNA encoding a CAR receptor or a fragment or analog thereof positioned for expression is the cell; (b) culturing the transformed cell under conditions for expressing the DNA; and (c) isolating the recombinant CAR receptor polypeptide.

In yet another aspect, the invention features a substantially pure antibody which specifically binds a CAR receptor polypeptide of the invention.

In yet other aspects, the invention features therapeutic compositions which include as an active ingredient a CAR receptor polypeptide of the invention formulated in a physiologically-acceptable carrier. Such therapeutic compositions may be used in methods of treating Graves' disease or cancer (for example, lung cancer) in a mammal; such methods involve administering the therapeutic composition to the mammal in a dosage effective to decrease thyroid hormone receptor function (for the treatment of Graves' disease) or in a dosage effective to increase retinoic acid receptor expression (for the treatment of cancer).

In yet other aspects, the invention features methods of identifying a CAR ligand. One method involves (a) providing a nucleic acid sequence which encodes a CAR receptor polypeptide; (b) introducing into a host cell which is functionally deficient for CAR receptor (i) the nucleic acid which encodes the CAR receptor polypeptide (preferably, a CAR receptor polypeptide including an amino acid sequence substantially identical to the amino acid sequence shown in FIG. 1; SEQ ID NO: 10) and (ii) a reporter gene operably linked to a CAR receptor polypeptide binding site (preferably, the binding site GGGTAGGGTTCAC-CGAAAGTTCACTCG; SEQ ID NO: 5); (c) measuring induction of the reporter gene in the transfected host cell; (d) contacting the transfected host cell with a candidate ligand; and (e) measuring induction of said reporter gene in the presence of the candidate ligand, an increase or decrease in the induction as compared to the induction in (c) being indicative of the presence of a CAR ligand.

The second method involves (a) providing a nucleic acid sequence which encodes a CAR receptor polypeptide (preferably, including an amino acid sequence substantially identical to the amino acid sequence shown in FIG. 1; SEQ ID NO: 10); (b) introducing the nucleic acid into a host cell so that the recombinant CAR receptor polypeptide is expressed; (c) isolating the recombinant protein; (d) immobilizing the recombinant protein on a solid substrate (preferably, a column); (e) contacting the immobilized recombinant protein with a candidate ligand under conditions which allow formation of an affinity complex between the immobilized recombinant CAR receptor polypeptide and the candidate ligand; and (f) detecting complex formation as an indication of the presence of a CAR ligand.

In yet other aspects, the invention features methods of identifying a CAR receptor DNA binding site. One method involves (a) providing a nucleic acid sequence which encodes a CAR receptor polypeptide (preferably including an amino acid sequence substantially identical to the amino acid sequence shown in FIG. 1; SEQ ID NO: 10); (b) introducing into a host cell which is functionally deficient for CAR receptor (i) the nucleic acid which encodes the CAR receptor polypeptide and (ii) a reporter gene which is operably linked to a candidate CAR receptor DNA binding site; and (c) measuring induction of the reporter gene in the transfected host cell, induction being indicative of the presence of an operably linked CAR receptor DNA binding site.

A second method involves (a) providing a nucleic acid sequence which encodes a CAR receptor polypeptide (preferably, including an amino acid sequence substantially identical to the amino acid sequence shown in FIG. 1; SEQ ID NO: 10); (b) introducing the nucleic acid into a host cell so that the recombinant CAR receptor polypeptide is expressed; (c) isolating the recombinant protein; (d) contacting the recombinant protein with a candidate DNA binding site under conditions which allow formation of an affinity complex between the recombinant CAR receptor polypeptide and the candidate binding site; and (e) detecting complex formation as an indication of the presence of a CAR receptor DNA binding site.

In a final aspect, the invention features chimeric receptors. Such chimeric receptors may include the DNA binding domain of a CAR receptor polypeptide (preferably, including a sequence substantially identical to amino acids 1–75 of FIG. 1; SEQ ID NO: 1 or a DNA binding fragment thereof) fused to the gene activation (and, preferably, the ligand binding domain) of a heterologous protein, preferably, a nuclear hormone receptor, or a protein chosen from the group consisting of: glucocorticoid receptor, α-retinoic acid receptor, β-retinoic acid receptor, γ-retinoic acid receptor, estrogen receptor, progesterone receptor, vitamin D receptor, mineralocorticoid receptor, thyroid receptor, VP16, and GAL4; or the chimeric receptor may include the gene activation domain of a CAR receptor polypeptide (preferably, including a sequence substantially identical to amino acids 76–348 of FIG. 1; SEQ ID NO: 10, or a gene activating fragment thereof) fused to the DNA binding domain of a heterologous protein, preferably, a nuclear hormone receptor or a protein chosen from the group consisting of: glucocorticoid receptor, α-retinoic acid receptor, β-retinoic acid receptor, γ-retinoic acid receptor, estrogen receptor, progesterone receptor, vitamin D receptor, mineralocorticoid receptor, thyroid receptor, and GAL4.

By "CAR receptor polypeptide" is meant a polypeptide which is capable of binding to a DNA sequence of GGG-TAGGGTTCACCGAAAGTTCACTCG (SEQ ID NO: 5) and activating the expression of downstream genes, even when mammalian cells harboring the receptor are grown in medium containing charcoal-stripped serum; in particular, a CAR receptor polypeptide activates such gene expression in the absence of retinoic acid.

By "substantially pure" is meant that the CAR receptor polypeptide provided by the invention is at least 60%, by weight, free from the proteins and naturally-occurring organic molecules with which it is naturally associated. Preferably, the preparation is at least 75%, more preferably at least 90%, and most preferably at least 99%, by weight, CAR receptor polypeptide. A substantially pure CAR receptor polypeptide may be obtained, for example, by extraction from a natural source (e.g., a mammalian liver cell); by expression of a recombinant nucleic acid encoding a CAR receptor polypeptide, or by chemically synthesizing the protein. Purity can be measured by any appropriate method, e.g., column chromatography, polyacrylamide gel electrophoresis, or HPLC analysis. By a "polypeptide" is meant any chain of amino acids, regardless of length or post-translational modification (e.g., glycosylation)

By "substantially identical" is meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein or domain (assayed, e.g., as described herein). A "substantially identical" nucleic acid sequence codes for a substantially identical amino acid sequence as defined above.

By a "DNA binding domain" is meant a stretch of amino acids which is capable of directing specific polypeptide (e.g., receptor) binding to a particular DNA sequence.

By "gene activation domain" is meant a stretch of amino acids which is capable of inducing the expression of a gene to whose control region it is bound.

By "heterodimerization domain" is meant a stretch of amino acids which is capable of directing specific complex formation with a heterologous protein; such a domain may direct the formation of dimers, trimers, tetramers, or other higher order hetero-oligomers.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "transformed cell" is meant a cell into which (or into an ancestor of which) has been introduced, by means of recombinant DNA techniques, a DNA molecule encoding (as used herein) a CAR receptor polypeptide.

By "positioned for expression" is meant that the DNA molecule is positioned adjacent to a DNA sequence which directs transcription and translation of the sequence (i.e., facilitates the production of, e.g., CAR receptor polypeptide).

By "a host cell which is functionally deficient for CAR receptor" is meant a cell, e.g., a mammalian cell, which exhibits little or no CAR receptor-mediated gene stimulatory activity; such activity may be measured in standard transactivation assays using, e.g., a transfected reporter gene operably linked to a CAR binding site as described herein.

By "substantially pure antibody" is meant antibody which is at least 60%, by weight, free from the proteins and naturally-occurring organic molecules with which it is naturally associated. Preferably, the preparation is at least 75%, more preferably at least 90%, and most preferably at least 99%, by weight, antibody, e.g., CAR receptor-specific antibody. A substantially pure CAR receptor antibody may be obtained, for example, by affinity chromatography using recombinantly-produced CAR receptor polypeptide and standard techniques.

By "specifically binds" as used herein, is meant an antibody which recognizes and binds CAR receptor polypeptide but which does not substantially recognize and bind other molecules in a sample, e.g., a biological sample, which naturally includes CAR receptor polypeptide.

By "reporter gene" is meant a gene whose expression may be assayed; such genes include, without limitation, chloramphenicol transacetylase (CAT) and β-galactosidase.

By "operably linked" is meant that a gene and a regulatory sequence(s) are connected in such a way as to permit gene expression when the appropriate molecules (e.g., transcriptional activator proteins) are bound to the regulatory sequence(s).

By "heterologous" is meant any protein other than the human CAR receptor which includes a suitable (i.e., a DNA binding, gene activation, and/or ligand binding) domain.

Other features and advantages of the invention will be apparent from the following description of the preferred embodiments thereof, and from the claims.

BRIEF DESCRIPTION OF THE DRAWING

FIG. 1 is the nucleic acid sequence and deduced amino acid sequence of the human CAR receptor (SEQ ID NO: 1 and 10).

DETAILED DESCRIPTION OF THE INVENTION

There now follows a description of the cloning and characterization of a human CAR receptor-encoding cDNA useful in the invention. This example is provided for the purpose of illustrating the invention, and should not be construed as limiting.

Isolation of the CAR Receptor

A human liver cDNA library was screened by standard techniques with the following degenerate oligonucleotide probe: TG C/T GAG GGI TG C/T AAG G G/C ITT C/T TT C/T A/C G (SEQ ID NO: 2). This probe was based on the sequence of the P box of the thyroid/retinoid receptor subgroup, the most highly conserved portion of the DNA binding domain. As expected, a number of clones encoding previously described members of the nuclear receptor superfamily were isolated. Based on limited sequence analysis (by standard techniques), one clone that did not correspond to any previously reported cDNA was chosen for further analysis. The complete sequence of this cDNA is presented in FIG. 1 (SEQ ID NO: 1).

As indicated in FIG. 1, this cDNA encodes a protein of 348 amino acids that contains conserved features of the nuclear receptor superfamily in both the DNA binding (C) domain and the putative ligand binding/dimerization (E) domain. Because of the activities of this protein described below, it is called CAR (Constitutive Activator of Retinoic acid response elements). CAR is one of the smallest superfamily members, with the shortest known A/B domain.

As expected from the oligonucleotide used for screening, the sequence of the P box DNA binding specificity determining region of the first zinc finger placed CAR in the thyroid/retinoid group. CAR was not strongly related to any other superfamily member, but was most similar to the vitamin D receptor, sharing 42 identical amino acids out of 66 in the C domain (64%), and 61/152 in the E domain (40%). This is quite similar to the relationship between the thyroid hormone and retinoic acid receptors: TRβ and RARβ which share 60% and 40% sequence identity in the C and E domains, respectively. By comparison, the closely related human TRα and TPβ receptors share 90% and 85% identity in the C and E domain. CAR also shows significant similarity to the Drosophila melanogaster ecdysone receptor (62% in the C domain, 29% in the E domain), making it the third member of a divergent subgroup in the superfamily. Southern blot analysis (by standard techniques) indicated that CAR may not be a member of a closely related subgroup like the TRs and the RARs.

Like a number of other members of the superfamily, CAR has a relatively long 5' untranslated region that contains several AUGs upstream of the start of the open reading frame. The function of this region is unknown.

Northern blot analysis (using standard techniques) indicated that CAR mRNA is expressed in a variety of human tissues, but is most abundant in liver. Multiple RNA species were observed, but the nature of these different species is not clear. Based on the multiple products expressed by genes encoding other superfamily members, it may well reflect alternative splicing or promoter utilization. CAR mRNA is also observed in a number of human cell lines, including HepG2 (hepatoma), JEG-3 (choriocarcinoma), and HeLa.

Ligand-independent Transcriptional Activation by the CAR Ligand/dimerization Domain To study the function of the putative ligand binding domain of the orphan, a chimeric receptor consisting of the C-terminal D, E and F domains of CAR (i.e., approximately amino acids 76–172, 173–319, and 320–348 of the CAR sequence, respectively) fused to the N-terminal A/B and C domains of TRβ was generated (termed TR/CAR), along with a control hybrid with the A/B and C domains of TR and the D, E and F domain of the glucocorticoid receptor (TR/GR). Vectors expressing these chimeras or the intact TR were cotransfected into JEG3 cells (ATCC Accession No: HTB 36) with reporter plasmids containing T3REs (i.e., of sequence AAAGGTAAGATCAGGGACGTGACCGCAG; SEQ ID NO: 3) or GREs (from the MMTV promoter as described in Chandler et al., *Cell* 33:489, 1989) upstream of a reporter gene whose expression could be assayed. Transfections were carried out in the presence of serum treated with activated charcoal to remove T3 as well as other low molecular weight hydrophobic compounds that could act as CAR ligands.

Results from such an analysis revealed that both TR and the TR/GR chimera behaved as ligand-dependent transactivators, as expected. The relatively low but reproducible level of activation conferred by TR/GR is consistent with a previous report, and is thought to be a consequence of the absence from this hybrid of transcriptional activation domains present in the A/B domain of the intact GR and the F domain of the intact TR.

In contrast, the TR/CAR chimera activated expression of the T3RE containing reporter in the absence of any added ligand. This effect was not altered by addition of T3, estradiol, testosterone, retinoic acid, or dexamethasone, or by the addition of the orphan receptor ligand 25-hydroxy cholesterol. The constitutive activation conferred by this hybrid was substantial, corresponding to greater than 50% of the response of the intact TRβ. Similar results were observed with an analogous GR/CAR chimera in cotransfections with an MMTV/CAT reporter.

The activation conferred by the TR/CAR chimera in the presence of charcoal-stripped serum could be a consequence of either a direct, constitutive transcriptional activation function in the D, E or F domains of the orphan, or the presence of an uncharacterized ligand in the medium of the growing cells. To minimize the possibility of the presence of such a ligand in the media, the transfections were repeated in the absence of serum. Such conditions substantially reduced the level of both control and T3-activated expression, but did not prevent the constitutive activation function conferred by the TR/CAR chimera. Because of the substantial changes in the levels of expression from control promoters, the significance of the apparent decrease in constitutive activity relative to the level of activation conferred by TRβ in the presence of hormone is uncertain. This apparent decrease may reflect the absence of some specific stimulator of CAR function present in serum or could be a less specific effect associated with the unfavorable growth conditions.

Activation of Retinoic Acid Response Elements by CAR

Based on the constitutive activity of the TR/CAR chimera and the similarity of the DNA binding domain of CAR to other members of the superfamily, a number of response elements were screened for activation by the intact orphan in standard cotransfections. Despite the relatively close sequence relationship between CAR and the vitamin D receptor, no response was seen with the combined vitamin D/RA response element from the rat osteocalcin gene (i.e., of sequence TGGGTGAATGAGGACATTACTGAC-CGCTCCG; SEQ ID NO: 4). However, CAR did transactivate two wild type elements, the RAREs from the RARβ gene and the alcohol dehydrogenase (ADH) gene (i.e., GGGTAGGGTTCACCGAAAGTTCACTCG; SEQ ID NO: 5). RAREs which were not transactivated by CAR included a potent up mutant version of the rat growth hormone gene T3RE/RARE (i.e., of sequence AAAGGTAAGATCAGG-GACGTGACCTCAG; SEQ ID NO: 6; in tandem copies with the second copy inverted; described in Brent et al., *Mol. Endocrinol.* 3:1996, 1989) and the wild type version of the laminin T3RE/RARE (i.e., of sequence AGACAGGT-TGACCCTTTTTCTAAGGGCTTAAC-CTAGCTCACCTG; SEQ ID NO: 8). The rat malic enzyme T3RE (i.e., of sequence AGGACGTTGGGGTTAGGG-GAGGACAGTG; SEQ ID NO: 9) and the rat α-myosin heavy chain T3RE (i.e., of sequence CTGGAGGTGACAG-GAGGACAGCAGCCCTGA; SEQ ID NO: 7), which do not respond to RARs, did not respond to CAR.

The activation of the RARβ element by CAR is not affected by several treatments that activate or inactivate signal transduction pathways mediated by protein kinases A or C. Thus, CAR activation was not altered by addition of dibutyryl cyclic AMP, by short or long term treatments with phorbol esters, or by cotransfections with vectors expressing the specific protein kinase A inhibitor peptide.

The activation of the RAREs by CAR suggests that this orphan could play an important role in the complex regulatory network that controls expression of RA responsive genes. To examine the functional interactions between CAR and RARβ, expression vectors for both were mixed in cotransfections. Increasing amounts of the CAR expression vector were added to a βRARE (SEQ ID NO: 5)-containing CAT reporter plasmid and a fixed amount of RARβ expression vector corresponding to approximately ⅔ of the level that is saturating for induction. In the absence of RA, the increasing amount of CAR led to an increase in basal expression. In the presence of RA, the high level of activated expression was not strongly affected by addition of CAR. Together, these effects resulted in a significant decrease in the RA induction ratio with increasing amounts of CAR.

These results indicate that the two superfamily members function independently at this response element. Analogous results were obtained when increasing amounts of RARβ were added to a subsaturating amount of CAR expression vector. In the absence of RA, the constitutive activation conferred by CAR could be blocked by excess RARβ. This is consistent with previous reports that RARs can repress expression in the absence of ligand. When retinoic acid was added, activation was observed at even moderate levels of RARβ. The levels of activated expression associated with the various doses of RARβ vector were similar to those observed in the absence of cotransfected CAR. It therefore seems most likely that CAR and RARβ do not interfere with each other when co-expressed at moderate levels. Under other circumstances, more complex indirect effects could be anticipated for the interaction between CAR and RXR (see below).

In contrast, addition of low levels of RXRα stimulated the effect of a subsaturating dose of CAR expression vector. Since similar results are observed with the receptors able to heterodimerize with RXRs, this result strongly suggests that RXRα may share a similar interaction with CAR.

DNA Binding by CAR

To confirm that CAR binds the βRARE, nuclear extracts from HeLa cells infected with vaccinia virus vectors overexpressing FLAG® epitope-tagged versions of CAR or RARα were used in standard gel shift experiments. Both CAR- and RARα-containing extracts showed specific binding to the RARβ element (SEQ ID NO: 5), with RAR binding being of higher apparent affinity. .In agreement with results of cotransfections, CAR binding was strongly stimulated by addition of nuclear extract from vaccinia infected HeLa cells overexpressing RXRα. However, little or no effect on affinity was observed when CAR and RAR were mixed. No evidence for formation of CAR/RAR heterodimers was observed in gels electrophoresed for longer times to better resolve the CAR and RAR shifted complexes. From these results, it appears that CAR can bind directly to the RARβ element, and that binding is strongly stimulated by RXRα.

The constitutive activity of CAR may be due to either a truly constitutive transcriptional activation function or the presence of some ubiquitous ligand. The former possibility is supported by its activity in serum free media and in distinct cell types. The existence of a ligand may be favored by the somewhat lower relative activity observed with serum free medium compared to medium containing charcoal stripped serum. However, the substantial changes in the expression of the control and activated promoters under these two quite distinct growth conditions suggest that less specific or direct effects could explain this difference.

Negative results have been obtained by several approaches designed to determine whether the constitutive activation of CAR is associated with various second messenger pathways. Evidence obtained to date indicates that CAR function is not affected by activation or repression of the activity of protein kinases A or C.

Based on the results presented here, it is possible that CAR plays two important roles in the complex, interlocking set of proteins that determines responses to RA, T3 and vitamin D. The first is to maintain a basal level of expression of a subset of RA responsive genes in the absence of the ligand. In the case of a cell expressing only RARβ, for example, this could allow expression of sufficient levels of the receptor to allow autoactivation of the RA-dependent positive feedback loop that regulates RARβ expression upon addition of ligand. The second potential function, is based on the interaction of CAR with RXR. Increasing expression of CAR would be expected to decrease the amount of RXR available for interaction with other heterodimeric partners. Thus, in a cell with limiting amounts of RXR, alterations in the amount or activity of CAR protein could have significant effects on the activity of RARs, T3Rs or VDR. Although the levels of CAR used in the cotransfections reported here did not show an antagonistic effect on RAR activity, preliminary results indicate that inhibitory effects of this type can be observed in other circumstances. Given the remarkable complexity of the regulatory networks that control response to the retinoids and the other ligands of this subgroup of the nuclear receptor superfamily, it is likely that even more complicated functions will be found for CAR.

Polypeptide Expression

Polypeptides according to the invention may be produced by transformation of a suitable host cell with all or part of a CAR receptor-encoding cDNA fragment (e.g., the cDNA described above) in a suitable expression vehicle.

Those skilled in the field of molecular biology will understand that any of a wide variety of expression systems may be used to provide the recombinant receptor protein. The precise host cell used is not critical to the invention. The CAR receptor may be produced in a prokaryotic host (e.g., *E. coli*) or in a eukaryotic host (e.g., *Saccharomyces cerevisiae* or mammalian cells, e.g., COS 1, NIH 3T3, and JEG3 cells). Such cells are available from a wide range of sources (e.g., the American Type Culture Collection, Rockland, Md.; also, see, e.g., Ausubel et al., *Current Protocols in Molecular Biology*, John Wiley & Sons, New York, 1989). The method of transfection and the choice of expression vehicle will depend on the host system selected. Transformation and transfection methods are described, e.g., in Ausubel et al. (*Current Protocols in Molecular Biology*, John Wiley & Sons, New York, 1989); expression vehicles may be chosen from those provided, e.g., in *Cloning Vectors*: A Laboratory Manual (P. H. Pouwels et al., 1985, Supp. 1987).

One preferred expression system is the mouse 3T3 fibroblast host cell transfected with a pMAMneo expression vector (Clontech, Palo Alto, Calif.). pMAMneo provides: an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding a CAR receptor polypeptide would be inserted into the pMAMneo vector in an orientation designed to allow expression. The recombinant receptor protein would be isolated as described below. Other preferable host cells which may be used in conjunction with the pMAMneo expression vehicle include COS cells and CHO cells (ATCC Accession Nos. CRL 1650 and CCL 61, respectively).

Alternatively, a CAR receptor polypeptide is produced by a stably-transfected mammalian cell line.

A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the receptor polypeptide is cloned into an expression vector which includes the dihydrofolate reductase (DHFR) gene. Integration of the plasmid and, therefore, the CAR receptor-encoding gene into the host cell chromosome is selected for by inclusion of 0.01–300 μM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHRF and pAdD26SV(A) (described in Ausubel et al., supra). Any of the host cells described above or, preferably, a DHFR-deficient CHO cell line (e.g., CHO DHFR⁻ cells, ATCC Accession No. CRL 9096) are among the host cells preferred for DHFR selection of a stably-transfected cell line or DHFR-mediated gene amplification.

Once the recombinant CAR receptor polypeptide is expressed, it is isolated, e.g., using affinity chromatography. In one example, a CAR binding site (e.g., the βRARE site described above) or an anti-CAR receptor antibody (e.g., produced as described below) may be attached to a column and used to isolate the receptor polypeptide. Lysis and fractionation of receptor-harboring cells prior to affinity chromatography may be performed by standard methods (see, e.g., Ausubel et al., supra). Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980).

Receptors of the invention, particularly short receptor fragments, can also be produced by chemical synthesis (e.g., by the methods described in *Solid Phase Peptide Synthesis*, 2nd ed., 1984 The Pierce Chemical Co., Rockford, Ill.).

These general techniques of polypeptide expression and purification can also be used to produce and isolate useful CAR receptor fragments or analogs (described below).

Identification of Ligands which Bind CAR Receptors

Although the CAR receptor described above was capable of activating some level of target gene expression in the apparent absence of a ligand, this does not discount the possibility that the receptor interacts with one or more ligands, e.g., to modulate receptor activity. Moreover, it is possible that multiple CAR receptors exist (e.g., as the products of a differentially-spliced CAR mRNA) and that different receptor species interact with different ligands. Accordingly, one aspect of the invention features a screening assay for the identification of compounds which specifically bind to the CAR receptors described herein. Such an assay may be carried out using a recombinant receptor protein.

In one example, the CAR receptor component is produced by a cell that naturally produces substantially no receptor or by a cell which produces functionally deficient receptor (i.e., a cell which apparently expresses CAR receptor mRNA as measured by Northern blotting but which does exhibit reporter gene induction, in the absence of recombinantly-produced CAR receptor, in a transactivation assay, see below); suitable cells are, e.g., those discussed above with respect to the production of recombinant receptor, most preferably, mammalian cells such as JEG3 cells. Host cells are transfected with (1) a vector which expresses a nucleic acid encoding the CAR receptor component (i.e., the "producer vector") and (2) a vector which includes a CAR receptor binding site (e.g., the βRARE sequence GGG-TAGGGTTCACCGAAAGTTCACTCG; SEQ ID NO: 5; described above) positioned upstream of a target gene which may be assayed (e.g., a CAT gene or a β-galactosidase gene) (i.e., the "reporter vector"). Using such a standard transactivation assay procedure, CAR receptor activity is assayed by measuring CAR binding site-dependent target gene expression. CAR ligands are identified as those compounds which, when added to the host cell medium, effect a change in CAR receptor-directed gene expression (as detected using any CAR reporter vector); a CAR ligand according to the invention may either increase CAR receptor activity or decrease CAR receptor activity.

Any suitable transactivation technique, CAR receptor-encoding producer vector, and CAR receptor binding site-containing reporter vector may be used. Descriptions of transactivation assays and generally useful vectors for the identification of ligands which bind other nuclear hormone receptors are described, e.g., in Evans et al. (U.S. Pat. No. 4,981,784, 1991); Evans et al. (WO 90/07517); Evans et al. (WO90/01428); and WO88/03168; all hereby incorporated by reference. CAR receptor polypeptides which may be used to screen for CAR ligands include wild-type molecules as well as any appropriate chimeric receptor, for example, the GR/CAR and TR/CAR receptors described above.

Candidate ligands may be purified (or substantially purified) molecules or the ligand may be one component of a mixture of ligands (e.g., an extract or supernatant obtained from cells; Ausubel et al., supra). In a mixed ligand assay, the CAR ligand is identified by testing progressively smaller subsets of the ligand pool (e.g., produced by standard purification techniques, e.g., HPLC or FPLC) until a single ligand is finally demonstrated to modulate the CAR receptor gene stimulatory activity. Candidate CAR ligands include peptide as well as non-peptide molecules.

Alternatively, a ligand may be identified by its ability to bind a CAR receptor polypeptide using affinity chromatography. Recombinant receptor is purified by standard techniques, from cells engineered to express the receptor (e.g., those described above); the recombinant receptor immobilized on a column (e.g., a Sepharose column or a streptavidin-agarose column by the immunoaffinity method of Ausubel et al., supra) and a solution containing one or more candidate ligands is passed through the column. Such a solution (i.e., such a source of candidate ligands) may be, e.g., a cell extract, mammalian serum, or growth medium on which mammalian cells have been cultured and into which the cells have secreted factors (e.g., growth factors) during culture; again, candidate CAR ligands include peptide as well as non-peptide molecules. A ligand specific for a recombinant receptor is immobilized on the column (because of its interaction with the receptor). To isolate the ligand, the column is first washed to remove non-specifically bound molecules, and the ligand of interest is then released from the column and collected.

CAR ligands isolated by the above methods (or any other appropriate method) may, if desired, be further purified (e.g., by high performance liquid chromatography; see above). Once isolated in sufficiently-purified form, a novel peptide ligand may be partially sequenced (by standard amino acid sequencing techniques). From this partial amino acid sequence, a partial nucleic acid sequence is deduced which allows the preparation of primers for PCR cloning of the ligand gene (e.g., by the method of Ausubel et al., supra).

Identification of CAR Receptor DNA Binding Sites

Identification of the CAR receptor facilitates identification of its DNA binding site(s). According to one approach, CAR receptor DNA binding sites may be identified using a transactivation assay, e.g., as described above for the identification of the binding site of sequence GGGTAGGGT-TCACCGAAAGTTCACTCG (SEQ ID NO: 5). Briefly, candidate DNA binding sites are inserted upstream of a target gene (whose expression may be assayed, e.g., those genes described above) and the ability of a CAR receptor polypeptide to bind the DNA site is assayed as its ability to activate downstream gene expression.

Alternatively, a DNA binding site may be identified by selectively retaining a receptor-bound DNA fragment on a nitrocellulose filter. This approach relies on the ability of nitrocellulose to bind proteins but not double-stranded DNA. Purified CAR receptor polypeptide (e.g., purified by standard techniques from cells engineered to express the receptor, e.g., those described above) is mixed with labelled double-stranded DNA (e.g., a random pool of DNA fragments) under conditions which allow interaction. After incubation, the mixture is suction filtered through nitrocellulose, allowing unbound DNA to pass through the filter while retaining the protein and any DNA specifically bound to it. Bound DNA fragments are then eluted from the filter and analyzed by gel electrophoresis or amplification and cloning. A detailed description of this technique is published in Ausubel et al., supra).

Candidate DNA fragments for either approach may be derived from a randomly cleaved or sonicated genomic DNA library and/or may be derived from known nuclear hormone response elements (see, e.g., Evans et al., WO90/11273).

Identification of CAR receptor DNA binding sites facilitates a search for the presence of such sites upstream of known or yet unidentified genes (e.g., by an examination of sequences upstream of known genes or by standard hybridization screening of a genomic library with binding site probes). CAR-mediated transcriptional control of genes bearing the binding site upstream may then be investigated (e.g., by transactivation experiments as described above), potentially leading to the elucidation of novel CAR receptor functions.

Chimeric Receptors

The functional domains of the CAR receptor may be swapped with the domains of other members of the nuclear hormone receptor family (see, e.g., Evans et al., WO 90/11273; Evans, Science 240:889, 1988) in order to produce receptors having novel properties. For example, if the DNA binding domain of the glucocorticoid receptor were fused to the gene activation domain of the CAR receptor, a novel receptor would be produced which could bind genes bearing an upstream glucocorticoid response element and activate gene expression in the absence of hormone. Conversely, fusion of the CAR DNA binding domain to the ligand-binding and gene activation domains of glucocorticoid receptor would confer hormonal regulation on genes downstream of CAR binding sites. Finally, fusion of the CAR DNA binding domain to a trans-repressing domain (see, e.g., Evans et al., WO90/14356) would result in repression of the basal level of expression of genes bearing upstream CAR binding sites. Construction of receptor fusion genes is carried out by standard techniques of molecular biology. CAR receptor domains are as follows: DNA binding domain, approximately amino acids 11–76; and gene activation and potential ligand binding domain, approximately amino acids 76–348. Examples of receptor domains which may be included in a chimeric CAR receptor are described in Evans et al. (WO 90/15815) and in Evans et al. (Science 240:889, 1988).

Dominant Negative Mutants

Mutants of the CAR receptor may be generated which interfere with normal CAR receptor activity. Such mutants are termed "dominant negative" and fall into at least two classes: (a) ones which bind to their DNA binding site (thereby interfering with the ability of wild-type receptor to bind the same site) and which do not activate gene expression and (b) ones which heterodimerize with other receptors (e.g., RXR) but which do not promote the biological response associated with the wild-type heterodimer.

The first class of CAR dominant negative mutants include those receptor polypeptides which contain a wild-type DNA binding domain and a mutant gene activation domain. Such mutants are unable to transactivate a reporter gene (e.g., as measured using a CAT reporter gene with an upstream βRARE and the standard methods described above) but retain the ability to bind a CAR DNA binding site (as evidenced, e.g., by DNA footprint analysis using a βRARE DNA sequence; Ausubel et al., supra).

The second class of CAR dominant negative mutants include those receptor polypeptides which contain a wild-type heterodimerization domain. Such a mutant interacts with its heterodimer partner and disrupts the partner's function. In one particular example, a dominant negative CAR receptor polypeptide may be overproduced (e.g., by directing its expression from a very strong promoter); the abundant CAR receptor polypeptide forms heterodimers with cellular RXR protein, soaking up available RXR and thereby preventing RXR homodimer formation as well as RXR heterodimer formation with other partner proteins (e.g., RAR, VDR, and T3R). Wild-type CAR receptor polypeptide may function as a dominant negative mutant if overproduced in this manner. However, a mutant CAR receptor lacking a gene activation domain (e.g., as identified above) and/or a DNA binding domain (e.g., as identified by DNA footprint analysis, above) is preferred.

Any of the above mutants may be generated by any method of random or site-directed DNA mutagenesis (see, e.g., Ausubel et al., supra).

Identification of Molecules which Modulate CAR Receptor Expression

Isolation of the CAR receptor gene also facilitates the identification of molecules which increase or decrease CAR receptor expression, and which may be useful as therapeutics, e.g., for treatment of cancers such as lung cancer, or for treatment of thyroid disorders such as Graves' disease. According to one approach, candidate molecules (e.g., peptide or non-peptide molecules found, e.g., in a cell extract, mammalian serum, or growth medium on which mammalian cells have been cultured) are added at varying concentrations to the culture medium of cells which express CAR receptor mRNA (e.g., HepG2, JEG-3, or HeLa cells). CAR receptor expression is then measured by standard Northern blot analysis (Ausubel et al., supra) using CAR receptor cDNA as a hybridization probe. The level of CAR receptor expression in the presence of the candidate molecule is compared to the level measured for the same cells in the same culture medium but in the absence of the candidate molecule. A molecule which promotes an increase or decrease in CAR receptor expression is considered useful in the invention.

Anti-CAR Receptor Antibodies

Human CAR receptor (or immunogenic receptor fragments or analogues) may be used to raise antibodies useful in the invention; such polypeptides may be produced by recombinant or peptide synthetic techniques (see, e.g., *Solid Phase Peptide Synthesis*, supra; Ausubel et al., supra). The peptides may be coupled to a carrier protein, such as KLH as described in Ausubel et al, supra. The KLH-peptide is mixed with Freund's adjuvant and injected into guinea pigs, rats, or preferably rabbits. Antibodies may be purified by peptide antigen affinity chromatography.

Monoclonal antibodies may be prepared using the CAR polypeptides described above and standard hybridoma technology (see, e.g., Kohler et al., *Nature* 256:495, 1975; Kohler et al., *Eur. J. Immunol.* 6:511, 1976;. Kohler et al., *Eur. J. Immunol.* :6:292, 1976; Hammerling et al., *In Monoclonal Antibodies and T Cell Hybridomas*, Elsevier, N.Y., 1981; Ausubel et al., supra).

Once produced, polyclonal or monoclonal antibodies are tested for specific CAR receptor recognition by Western blot or immunoprecipitation analysis (by the methods described in Ausubel et al., supra). Antibodies which specifically recognize a CAR receptor polypeptide are considered to be useful in the invention; such antibodies may be used, e.g., in an immunoassay to monitor the level of CAR receptor produced by a mammal.

Therapy

Because a lack of retinoic acid receptor has been associated with the occurrence of lung cancer and because the CAR receptor polypeptide binds and activates expression of the retinoic acid receptor gene, it is likely that the administration of a CAR receptor polypeptide to a mammal may prevent or treat cancers, particularly lung cancer. Similar therapeutic results would be expected for administration of a ligand which stimulates CAR receptor activity.

CAR receptor polypeptides may also find therapeutic use in the treatment of Graves disease, a disease resulting from an increase in thyroid hormone receptor function. RXR protein plays a role in thyroid hormone receptor expression. Accordingly, dominant negative CAR mutants which heterodimerize with RXR protein (including overexpressed wild-type CAR receptor protein) may act to decrease the cellular levels of available RXR and thereby decrease thyroid hormone receptor function. Again, ligands which increase heterodimerization efficiency could also be administered as a treatment for Graves' disease.

To treat the above diseases, the appropriate CAR receptor polypeptide (or ligand) is administered as a therapeutic preparation (e.g., in physiological saline) in accordance with the condition to be treated. Ordinarily, it will be administered intravenously, at a dosage effective to increase retinoic acid receptor expression (as a cancer treatment) or effective to decrease thyroid hormone receptor function (as a treatment for Graves' disease). Alternatively, it may be convenient to administer the therapeutic orally, nasally, or topically, e.g., as a liquid or a spray. Again, the dosages are as described above. Treatment may be repeated as necessary for alleviation of disease symptoms.

The methods of the invention may be used to reduce the disorders described herein in any mammal, for example, humans, domestic pets, or livestock. Where a non-human mammal is treated, the CAR receptor polypeptide or the antibody employed is preferably specific for that species.

Other Embodiments

Polypeptides according to the invention include the entire human CAR receptor (as described in FIG. 1; SEQ ID NO: 10) as well as any analog or fragment of the human CAR receptor which includes either a DNA binding domain and a gene activation domain; or which includes a heterodimerization domain (as identified using the techniques described above).

Polypeptides of the invention also include all mRNA processing variants (e.g., all products of alternative splicing or differential promoter utilization) as well as CAR receptor proteins from other mammals.

Specific receptor fragments or analogues of interest include full-length or partial (see below) receptor proteins including an amino acid sequence which differs only by conservative amino acid substitutions, for example, substitution of one amino acid for another of the same class (e.g., valine for glycine, arginine for lysine, etc.) or by one or more non-conservative amino acid substitutions, deletions, or insertions located at positions of the amino acid sequence which do not destroy the receptors' ability to either bind DNA and activate transcription; or to interact with CAR receptor's heterodimerization partners (as assayed above). Analogs also include receptor polypeptides which are modified for the purpose of increasing peptide stability; such analogs may contain, e.g., one or more desaturated peptide bonds or D-amino acids in the peptide sequence or the peptide may be formulated as a cyclized peptide molecule.

Other embodiments are within the following claims.

We claim:

1. A chimeric receptor comprising a DNA binding domain of a CAR receptor polypeptide which comprises amino acids 11–75 of FIG. 1 (SEQ ID NO: 10) fused to the gene activation domain of a heterologous protein.

2. The chimeric receptor of claim 1, wherein said heterologous protein is a nuclear hormone receptor.

3. The chimeric receptor of claim 1, wherein said heterologous protein is chosen from the group consisting of: glucocorticoid receptor, α-retinoic acid receptor, β-retinoic acid receptor, γ-retinoic acid receptor, estrogen receptor, progesterone receptor, vitamin D receptor, mineralocorticoid receptor, thyroid receptor, VP16, and GAL4.

4. The chimeric receptor of claim 1, wherein said receptor further comprises the ligand binding domain of a nuclear hormone receptor protein.

5. A chimeric receptor comprising a gene activation domain of a CAR receptor polypeptide which comprises amino acids 76–348 of FIG. 1 (SEQ ID NO: 10) fused to the DNA binding domain of a heterologous protein.

6. The chimeric receptor of claim 5, wherein said heterologous protein is a nuclear hormone receptor.

7. The chimeric receptor of claim 5, wherein said heterologous protein is chosen from the group consisting of: glucocorticoid receptor, α-retinoic acid receptor, β-retinoic acid receptor, γ-retinoic acid receptor, estrogen receptor, progesterone receptor, vitamin D receptor, mineralocorticoid receptor, thyroid receptor, and GAL4.

* * * * *

UNITED STATES PATENT AND TRADEMARK OFFICE
CERTIFICATE OF CORRECTION

PATENT NO. : 5,686,574
DATED : November 11, 1997
INVENTOR(S) : David D. Moore and Myriam I. Baes It is certified that error appears in the above-identified patent and that said Letters Patent is hereby corrected as shown below:

Title page,
Item [54], replace "RETINOID" with -- RETINOIC --;
Item [22], replace "Jun. 5, 1995" with -- Jun. 3, 1995 --; and Column 3,
Line 35, replace "1-75" with -- 11-75 --.

Signed and Sealed this

Eighteenth Day of March, 2003

JAMES E. ROGAN
*Director of the United States Patent and Trademark Office*

UNITED STATES PATENT AND TRADEMARK OFFICE
CERTIFICATE OF CORRECTION

PATENT NO. : 5,686,574
DATED : November 11, 1997
INVENTOR(S) : David D. Moore and Myriam I. Baes It is certified that error appears in the above-identified patent and that said Letters Patent is hereby corrected as shown below:

<u>Title page,</u>
Item [54], after "RESPONSE" insert -- ELEMENTS --.

Signed and Sealed this

Twenty-second Day of July, 2003

JAMES E. ROGAN
*Director of the United States Patent and Trademark Office*